Figure 1:
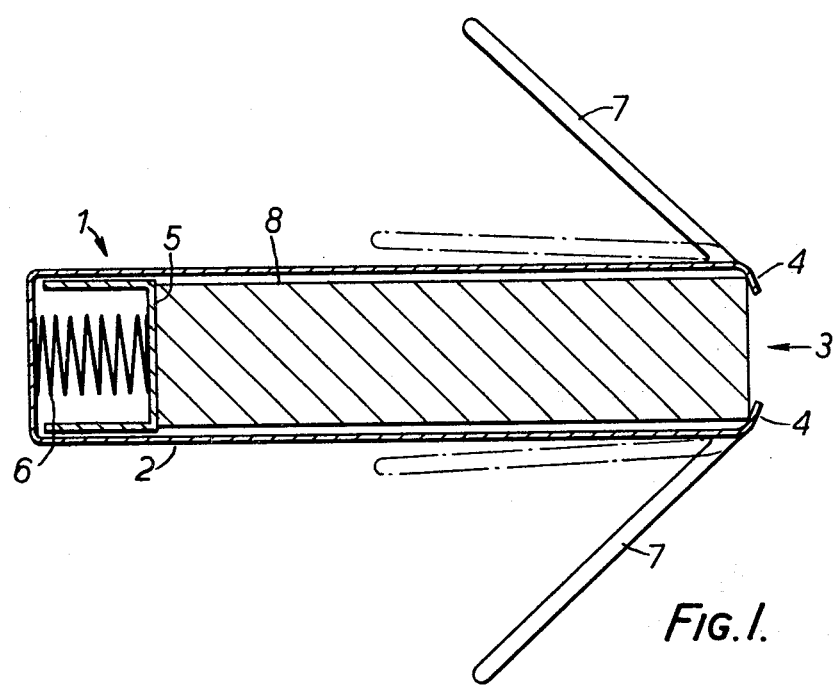

United States Patent [19]

Laby

[11] 4,251,506
[45] Feb. 17, 1981

[54] CONTROLLED-RELEASE COMPOSITIONS FOR ADMINISTRATION OF THERAPEUTIC AGENTS TO RUMINANTS

[75] Inventor: Ralph H. Laby, Canterbury, Australia

[73] Assignee: Commonwealth Scientific and Industrial Research Organization, Australia

[21] Appl. No.: 904,202

[22] Filed: May 9, 1978

[30] Foreign Application Priority Data

May 25, 1977 [AU] Australia .............. PD0230

[51] Int. Cl.² .............. A61K 9/22; A61K 9/26
[52] U.S. Cl. .............. 424/19; 424/22
[58] Field of Search .............. 424/14–22, 424/38

[56] References Cited

U.S. PATENT DOCUMENTS

| | | | |
|---|---|---|---|
| 3,056,724 | 10/1962 | Marston | 424/22 |
| 3,374,146 | 3/1968 | Blicharz et al. | 424/19 |
| 3,535,419 | 10/1970 | Siegrist et al. | 424/22 |
| 3,538,215 | 10/1970 | Snyder et al. | 424/38 |
| 3,655,864 | 4/1972 | Grass et al. | 424/38 |
| 3,670,065 | 6/1972 | Eriksson et al. | 424/19 |
| 3,696,189 | 10/1972 | Snyder | 424/38 |
| 3,857,933 | 12/1974 | Ross et al. | 424/20 |
| 3,926,817 | 12/1975 | Nakajima et al. | 424/22 |
| 3,959,493 | 5/1976 | Baalsrud et al. | 424/38 |
| 4,132,753 | 1/1979 | Blichare et al. | 424/38 |

FOREIGN PATENT DOCUMENTS

| | | | |
|---|---|---|---|
| 449029 | 3/1972 | Australia | 424/15 |
| 470538 | 11/1974 | Australia | 424/14 |

*Primary Examiner*—Shep K. Rose
*Attorney, Agent, or Firm*—Bacon & Thomas

[57] ABSTRACT

A controlled release composition for administering active agents to ruminants, which when mixed with said active agent has a melting point in excess of 39° C. and when inserted as a solid into the rumen of a ruminent, is capable of slowly disintegrating at the interface between said composition and ruminal fluid present in the rumen of said ruminant.

The composition may be administered by means of a variable geometry capsule.

9 Claims, 6 Drawing Figures

CONTROLLED-RELEASE COMPOSITIONS FOR ADMINISTRATION OF THERAPEUTIC AGENTS TO RUMINANTS

The present invention concerns controlled-release compositions for administration of therapeutic agents to ruminants and to variable geometry devices suitable for administration of the compositions to ruminants.

We have already described a depot capsule of a size and shape suited to administration per os to ruminants (e.g. sheep and cattle) which, after administration, can open to a size and shape that is too large to be regurgitated and is thus retained in the rumen throughout its useful life (Australian Patent No. 449,029). This depot device can be used to hold controlled release systems for antibloat detergents, magnesium to prevent grass tetany in cattle (Australian Patent Application No. 55556/73) and iodine to prevent hypothyroidism in sheep and cattle (Australian Patent Application No. 69779/74).

U.S. Pat. No. 3,857,933 discloses a controlled-release composition consisting of a glycol ester of a wax acid containing 22 to 39 carbon atoms and a physiologically tolerable surface-active substance present as an oil in water emulsifier in which the glycol ester is characterised by being sparingly soluble in the digestive tract. The therapeutic compositions described in the above U.S. patent specification are prepared by melting the ingredients of the composition, mixing them together and casting the molten mixture into small beads. When administered the therapeutic agent is slowly extracted from the beads by elution, as the beads pass through the gastro intestinal tract leaving behind an intact porous bead comprised of the sparingly soluble glycol ester. Such controlled-release compositions are only suited to therapeutic agents which are either water soluble or capable of dissolving in the surface-active substance. In addition, the rate of release of the therapeutic agent from such compositions decreases with time.

Advantages would therefore accrue to a composition, the whole of which is slowly disintegrated, particularly when used to administer a water insoluble therapeutic agent. In addition, the rate at which the therapeutic agent is made available from such a composition is determined by the rate at which the composition disintegrates and not the rate at which the therapeutic agent is dissolved from a sparingly soluble carrier.

Accordingly the present invention provides a controlled-release composition suitable for administering a therapeutic agent to ruminants, said composition when mixed with said therapeutic agent having a melting point in excess of 39° C. and which, when inserted as a solid into the rumen of a ruminant, is capable of slowly disintegrating at the interface between said composition and ruminal fluid present in the rumen of said ruminant.

The composition may comprise a biologically acceptable solid surfactant which is capable of slow dispersion in ruminal fluid such as those solid surfactants having an HLB value of 8.5 or less, for example, N,N-dihydroxyethyl octadecylamine, i.e. stearylamine ethoxylated with 2 moles of ethylene oxide, e.g. Teric 18M2 (Reg. Trade Mark). The rate at which N,N-dihydroxy ethyl octadecylamine is dispersed in ruminal fluid can be varied by esterification with either organic or inorganic acids. Other useful solid surfactants are cetyl alcohol ethoxylated with 2 moles of ethylene oxide, stearyl alcohol ethoxylated with 2 moles of ethylene oxide, polyoxyethylene sorbitol hexastearate, and sorbitan monostearate. These surfactants are known commercially by the names Brij 52, Brij 72, G1050 and Span 60 respectively. All are products of ICI (America) Limited.

A limited range of biologically safe surfactants suitable for use in this invention which are acceptable by national health regulatory bodies includes the surfactants just described, namely Brij 52, Brij 72, Span 60, G1050 but not Teric 18M2. The first four materials are not as well suited for use in the present invention as Teric 18M2 and are best used in mixtures which more or less reproduce the consistency of Teric 18M2. Generally a hard material, e.g. Span 60 or Tween, must be mixed with at least one of the soft materials, e.g, Brij 52, Brij 72 or Brij 80 (Sorbitan monooleate, a biologically safe liquid surfactant) to achieve the desired consistency, which is judged, for example, by a melting point range and penetrometer or other rheological measurement.)

By way of example, the following mixtures have been found satisfactory in in vivo trials.

Brij 72: 83%, Span 60: 17%
Brij 80: 40%, Span 60: 60%

It is important in choosing the components in such mixtures that in addition to their biologically acceptability, their HLB values should not differ markedly from each other, as this will lead to possible differential dissolution, the component with the higher HLB diffusing preferentially faster than that with the lower HLB. This can give rise to release rates of the active ingredient which are non uniform and in certain instances, this could lead to non reproducible performance and even complete stopping of release before exhaustion. Accordingly, in compositions containing mixed surfactant the HLB values should be similar and not differ by more than 2 units. In the cases cited, the HLB values for Brij 72, Span 60 and Brij 80 are respectively 4.9, 4.7 and 4.3.

The composition may also comprise a solid composition which is susceptible to erosion at the interface between the composition and ruminal contents. Erosion may be caused by direction action of the ruminal fluid on the composition, mechanical attrition at the interface as a result of the normal digestive action of the rumen, or a combination of both. Compositions comprised of a water insoluble wax and a non-ionic surfactant are capable of functioning in this way.

Accordingly the composition may comprise a biologically acceptable water insoluble wax, and a biologically acceptable nonionic surfactant, said composition being susceptible to erosion in the rumen of a ruminant. Normally the rate of erosion is controllable by variation of the constitution of said composition. The wax may be, for example, stearic acid, paraffin wax, beeswax or any other biologically acceptable wax. Suitable nonionic surfactants are the ethoxylated alcohols and polyether glycols, for example, Teric PE68, Teric 12A23 or Teric 16A29. "Teric" is the registered trademark of I.C.I. Australia Ltd. and the product numbers refer respectively to a block copolymer of polypropylene glycol having a molecular weight of 1750 ethoxylated to a molecular weight of 8,750; synthetic $C_{12-15}$ alcohol ethoxylated with 23 moles of ethylene oxide; and synthetic $C_{16-18}$ alcohol ethoxylated with 29 moles of ethylene oxide.

In binary compositions comprising a water insoluble wax and a nonionic surfactant, there is frequently a range of compositions over which small increases in the surfactant content drastically increase the solubility of the composition. However, by including a water soluble polymer in the composition such drastic changes can be decreased. Preferably, therefore, such binary compositions are modified by inclusion of a biologically acceptable water soluble polymer such as a polyethylene glycol having a molecular weight of 2000 or more.

The invention also provides therapeutic compositions comprising a mixture of a therapeutic agent and said controlled-release composition. The therapeutic composition functions by controlled disintegration thereof in the rumen.

The rate of release of the therapeutic agent from the therapeutic composition can be controlled in a number of ways. Firstly the rate of disintegration of the therapeutic composition can be increased or decreased by varying the components of the composition. Secondly the rate of release of the therapeutic agent may be varied by limiting the area of the therapeutic composition exposed to the rumen environment. In this case the rate of release is proportional to the area of exposed composition. Thirdly the rate of release of therapeutic agent from the composition can be varied by altering the concentration of therapeutic agent in the composition. Preferably however the therapeutic composition contains no more than 50% by weight of the therapeutic agent.

The therapeutic agent need not be uniformly distributed in the composition. For example, a succession of pulse doses can be delivered by making the therapeutic composition in such a way that it comprises layers of the composition containing the therapeutic agent interspersed between layers containing little or no therapeutic agent.

In a third aspect of the present invention there is provided a method of treating ruminants with a therapeutic composition which method comprises mixing a therapeutic agent with a biologically acceptable carrier to form a therapeutic composition having a melting point in excess of 39° C. and which, when inserted into the rumen of a ruminant, is capable of slowly disintegrating at the interface between said composition and ruminal fluid present in said rumen, and administering said composition to ruminants in such a manner that the composition is not regurgitated until substantially all said composition has disintegrated.

The therapeutic compositions of the present invention may be administered by means of the variable geometry capsules described in our U.S. Pat. No. 3,844,285, (especially in FIGS. 1 to 3 thereof) the complete disclosure of which is incorporated herein by reference.

Briefly, the capsules comprise at least one body portion containing or comprising said composition and having a first configuration or being adapted to be arranged in a first configuration, whereby it is adapted to be administered per os so as to pass into the rumen and being adapted to change in the rumen into a second configuration which will prevent or at least hinder regurgitation of the device, whereby the device is retained in the rumen.

In this case the therapeutic composition is poured molten into the capsule. After the therapeutic composition has hardened the capsule is administered as described in the above patent specification. When administered by this means it has been noted that disintegration occurs at the openings in the capsule where the composition is exposed to the rumen environment. The release rate usually declines with time as disintegrated composition is replaced in the capsule by rumen-derived solids which tend to act as a barrier to further disintegration. Uniform release of the therapeutic agent can be achieved when using this method of administration, by increasing the concentration of therapeutic agent with depth of composition below the exposed parts of the capsule in a manner that compensates for the decline in release rate of the composition.

Normally the therapeutic compositions of the present invention have a melting point in excess of 39° C. However, if the compositions are to be administered by means of the variable geometry capsules illustrates in the above patent, lower melting points can be tolerated providing however that the composition is not a free flowing liquid at 39° C., but a composition which was a gelatinous mass at this temperature would be tolerable.

In a further aspect of the invention there is provided a variable geometry device for administration of a solid therapeutic composition which device comprises a hollow body having an opening, a driving means for urging a solid therapeutic composition contained therein towards said opening, restricting means to prevent expulsion of the solid therapeutic composition therefrom by said driving means, a resilient member forming a first configuration with the body and which is capable of being resiliently deformed to provide a second configuration in which the device is capable of being administered to a ruminant per os, said resilient member being capable of reverting to the first configuration when the device reaches the rumen after administration thereof, said first configuration being such as to substantially reduce the possibility of regurgitation from said rumen. The variable geometry device may also include a means for inserting a precast plug of said therapeutic composition into the body. The driving means may be a sealed expandable body filled with a volatile liquid having vapour pressure in excess of 1 atmosphere at 39° C. The driving means may also be a plunger biased by a resilient body such as a weak helical spring, e.g. a spring which at full compression is capable of exerting a pressure in the range from 50 grams per square cm. to 500 grams per square cm.

Preferably the hollow body portion comprises a cylindrical tube open at one end, the other end having a base supporting a helical spring to which a plunger is attached which plunger is capable of being urged by the spring toward the opening.

The driving means may also comprise a small volume of a volatile liquid retained behind a close-fitting plunger which liquid has a vapour pressure in excess of one atmosphere at normal rumen temperatures. Trichlorofluoromethane, for example Monsanto's "Isceon No. 1" may be used. This has a boiling point of 23.8° C. and provides a vapour of 1.65 atmospheres at the rumen temperature of 39° C. However care must be taken in selecting the material for construction of the body when using trichlorofluoromethane. For example, trichlorofluoromethane diffuses through polypropylene and causes it to swell. Nylon can be used with trichlorofluoromethane. The preferred volatile liquid is however methyl formate which can be used with polypropylene as well as nylon.

The means for enabling a precast plug of the therapeutic composition to be inserted into the device may be provided by incorporating into the body of the device, a detachably secured base through which the plug and driving means can be inserted before the base is secured in position. Alternatively the restricting means may be of such flexibility that the plug can be manually pushed past the restricting means but of sufficient rigidity to overcome a force exerted by the driving means on the plug when the plug is in position.

Preferably the resilient member comprises one or more arms integrally moulded with the body in a resilient plastics material.

When the therapeutic composition is in position, the device is held with the resilient member in the second configuration and the device administered per os to a ruminant. On reaching the rumen the attachment reverts to the first configuration thereby preventing regurgitation of the device. Rumenal fluids enter the open end and cause the composition contained in the device to slowly disintegrate. As the composition progressively disintegrates, the driving means retains the composition in contact with the restricting means thereby preventing rumen derived solids from entering the device and thereby tending to act as a barrier to further disintegration. In this way the variable geometry device of the present invention provides a uniform rate of disintegration of the therapeutic composition.

The device and the controlled release composition of the present invention are particularly useful for administering anthelmintic agents to ruminants. For example, therapeutic compositions in which the therapeutic agent is oxfendazole (Syntex) are especially effective aganist *Ostertagia ostertagi* when administered by means of the device of the present invention. Administration of oxfendazole by means of the controlled release system of the present invention provides advantages over the normal method of administration which comprises strategic dosing. These advantages include in particular a more certain means of preventing type 2 Ostertagiasis which is a highly fatal consequence of the sudden emergence of large numbers of encysted inhibited 4th stages of Ostertagia, and also the potential for eliminating particular helminths from particular areas by means of complete inhibition of reproduction. Other anthelmintic agents may of course be used, such as Albendazole (Smith, Kline & French).

Other biologically active agents which can be administered in accordance with the principles of the invention include growth-stimulants, such as Monesin sodium (Eli Lilly & Co.), and Elfazepam (Smith, Kline & French) and chemical defleaing agents, such as dexamethazone and flumethazone.

The invention is also useful in administration of radioactively-labelled compounds for experimental purposes, for example, compounds used as fecal dry-matter markers in animal nutrition studies.

An embodiment of the device of the invention will now be described with reference to FIG. 1 of the accompanying drawings.

FIG. 1 is a cross sectional view of a variable geometry device according to the invention. The device 1 comprises a tubular body 2 having an opening 3 at one end, which opening is restricted by resilient projections 4. Preferably the body has a length of 14 cm. and a diameter of 2.8 cm. for cattle and a length of 9 cm. and a diameter of 1.6 cm. for sheep. The projections 4 protrude inwardly from said one end of the body. The other end of the body is closed. The body contains a cupped plunger 5 which is capable of sliding longitudinally thereof. The plunger is biased by means of a helical spring 6. The helical spring is made from spring steel wire having a circular transverse cross section of 0.5 mm. in diameter. The spring comprises 20 to 30 coils and is capable when fully compressed of exerting a pressure of approximately 100 grams per sq. cm. The body has two resilient arms 7 attached thereto at said one end, which arms project outwardly from said body at an angle of approximately 45° to the side thereof to form a first configuration. In the first configuration the device has the shape of an arrow-head. The arms 7 are capable of being resiliently flexed about an axis corresponding approximately with the junction of the arms with the body, to form a second configuration in which the arms are substantially parallel to the length of the body as shown by the dotted lines in FIG. 1. With the arms folded back into the second configuration the device is capable of being administered to cattle per os. As shown in FIG. 1, the body contains a precast cylindrical plug 8 of a therapeutic composition. The resilient projections 4 are sufficiently flexible to allow the precast plug to be inserted into the device but have sufficient rigidity to retain the plug within the device against the pressure exerted by the spring. Alternatively, a barrier preventing ejection of the plug by action of the spring can be applied after the plug has been inserted, e.g. a strip of polypropylene welded across the opening 3 of the body. The body 2, arms 7 and projections 4 may be integrally moulded from a suitable plastics material such as polyethylene polypropylene or nylon. By choice of the appropriate material of construction a device may be obtained which can be retained in the rumen indefinitely or for lesser periods of time. For example, a device integrally moulded from low density, low molecular weight polyethylene will eventually fail after about 270 days in the rumen by flex cracking of the arms. On the other hand, a device integrally moulded from polypropylene is virtually indestructable.

When therapeutic compositions having a matrix of N,N-dihydroxyethyl octadecylamine are administered by means of the variable geometry device of the present invention the composition imbibes ruminal fluid and swells thereby causing the composition to expand diametrically and prevent additional fluid from penetrating the space between the plug of therapeutic composition and the interior wall of the body. Thus only one end of the plug remains exposed to the rumen environment thereby ensuring a steady rate of disintegration.

By choice of a suitable spring the composition can be exposed to an urging force which just exceeds the critical yield stress of the composition thereby causing the composition to be slowly extruded and subjected to mechanical erosion. Alternatively, in a two or three component matrix in which one or two of the components are water dispersible, exposure to ruminal fluids will cause substantial swelling and softening of the matrix to occur resulting in extrusion and erosion of the composition as described above, or in some cases the matrix will be slowly compressed and the water dispersible component slowly expressed, together with the therapeutic agent entrained therein. On the other hand if the composition comprises one or more slowly water dispersible components mixed with one or more water insoluble components and the water dispersible components form a matrix in which the water insoluble components are dispersed, the composition will disintegrate by dispersion of the dispersible components in the ruminal fluid since these act as the binding agent for the composition. On the other hand the content of water insoluble components will determine the rate at which the composition disintegrates by this means.

The use of a device such as that described above to administer the composition of the invention places further restrictions on the compositions. For example, Brij 72 (Penetrometer reading at 39° C. of 3 to 4 kg cm$^{-2}$ at shear rates $2.8-7.0 \times 10^{-2}$ cm sec$^{-1}$) in capsules having a spring which at 75% compression exerts a force of 300 grams in cattle or 160 grams in sheep, will extrude spontaneously at much too high a rate and may actually extrude while the capsule is still in its packaging if placed in direct sun. The addition of Span 60 to provide a composition containing 17% Span 60 and 83% Brij 72 increases the penetrometer reading to 6 to 8 kg cm$^{-2}$ which works very satisfactorily.

Generally, it can be stated that when using the capsule of the invention the penetrometer reading of the surfactant should be between 5 and 40 kg cm$^{-2}$ for the shear rates quoted above.

It has also been discovered that when using compositions which seal against the sides of the device of the present invention, subsequent movement of the plug by action of the spring reduces gas pressure in the spring compartment and the movement of the plug is then determined by the rate at which gases (carbon dioxide in particular) diffuse through the composition. Thus, the uniformity of release (the most critical property of the spring driven capsule) is enhanced by the process of gas diffusion through the composition to the spring cavity behind the composition. In order to take advantage of this phenomenon the end of the spring cavity remote from the piston should be sealed and the plunger should be loose fitting, a clearance of 0.5 to 1 mm being satisfactory.

The invention will now be further described with reference to the accompanying examples.

EXAMPLE 1

Matrices made up of stearic acid, polyethyleneglycol M.W.=6000 and Teric 16A29 were poured molten into cylindrical containers open at one end. The containers were inserted in rumen fistulated cattle grazing mixed pasture and taken out at different times after insertion. The amount of matrix remaining in the containers was measured after drying at 100° C. under 700 mm vacuum. The results are given in Table I.

TABLE 1

| Composition, Stearic Acid | % PEG6000 | 16A29 | Rate, mg cm$^{-2}$ day$^{-1}$ at 8 days after insertion |
| --- | --- | --- | --- |
| 30 | 60 | 10 | 357 |
| 45 | 15 | 40 | 134 |
| 50 | 30 | 20 | 45 |

EXAMPLE 2

Figure 2:
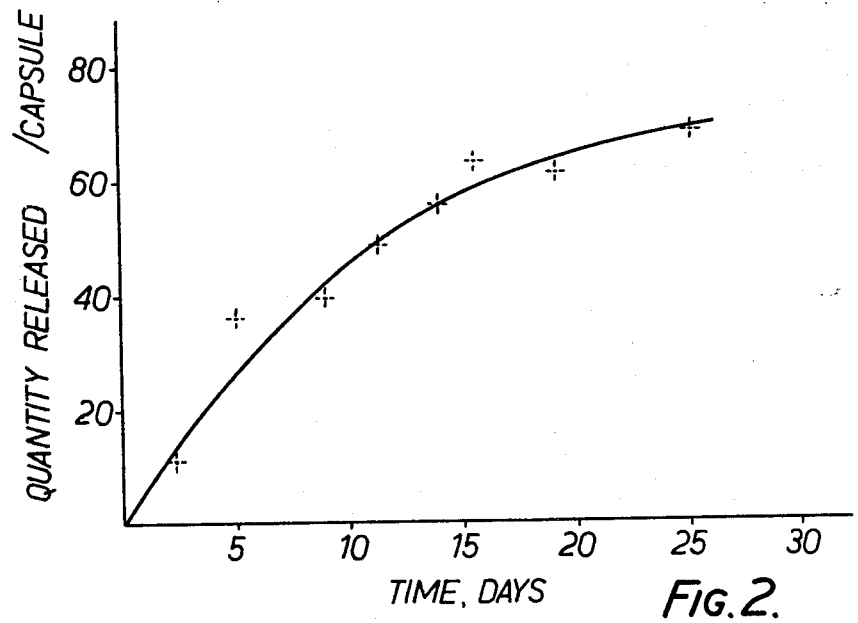
Figure 3:
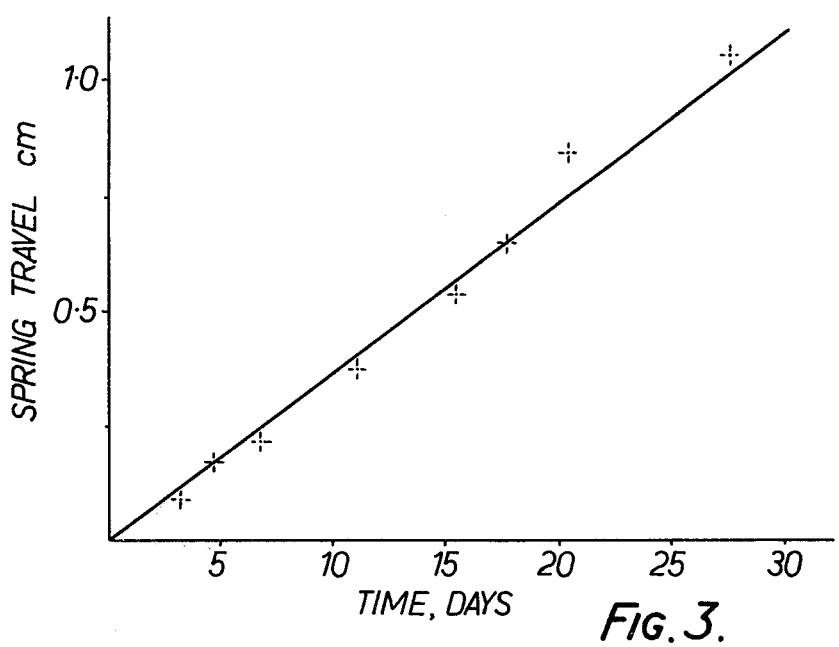

A matrix consisting of stearic acid (50%) polyethylene glycol M.W.=6000 (15%) and Teric 16A29 (35%) was poured molten into capsules of the type illustrated in FIGS. 1 to 3 of the complete specification of Australian Patent No. 499,029. The rate of dissolution of matrix was studied in vivo as for the cylindrical vessels of Example 1. The rate of release of matrix, r, g/capsule/day at time t is given in Table 2. The amount of matrix released, m, g/capsule with time is shown in FIG. 2.

TABLE 2

| r, g/capsule/day | t, day |
| --- | --- |
| 3.3 | 5 |
| 2.3 | 10 |
| 1.6 | 20 |
| 1.3 | 30 |
| 1.2 | 40 |
| 1.0 | 60 |

EXAMPLE 3

A cylindrical core of matrix consisting of stearic acid (50%) polyethylene glycol M.W.=6000 (15%) and Teric 16A29 (35%) having a diameter=2.5 cm and length=10 cm was inserted into a capsule of the type illustrated in FIG. 1 and the capsule placed in the rumen of a fistulated cow as in Examples 1 and 2. The release of matrix was followed by the measurement of spring extension, which is given in FIG. 3.

EXAMPLE 4

Variable geometry capsules of the type illustrated in FIGS. 1 to 3 of the complete specification of Australian Patent No. 449,029 were filled with a matrix consisting of stearic acid (32%) polyethyleneglycol M.W.=6000 (58%) and Teric 16A29 (10%). The matrix contained powdered Oxfendazole (0.71%) suspended therein. 6 capsules were inserted orally into 6 steers naturally infested with *Ostertagia ostertagi* the capsules released 0.26 mg/kg bodyweight per day during the trail. Other treatment groups for comparison were treated with 0.625, 1.25, 2.5 and 5.0 mg/kg bodyweight/day. All animals, including untreated controls, were killed 8 days after treatment for assessment of worm burden. Results are given in Table 2. % efficiency of the anthelmenthic effect is given by:

$$\frac{\text{control count - treated count}}{\text{control count}} \times 100$$

TABLE 2

| Treatment | Dose mg/kg | Adults | Anthelmenthic effect, 4th Stage | Early 4th Stage | % Total |
| --- | --- | --- | --- | --- | --- |
| Capsules | 0.26 × 8d | 68 | 57 | 80 | 74 |
| Single dose | 0.625 | 69 | 64 | 61 | 64 |
| | 1.25 | 87 | 66 | 48 | 63 |
| | 2.5 | 95 | 88 | 82 | 87 |
| | 5.0 | 97.5 | 92 | 87 | 91 |

The relatively efficient kill of the early 4th stage larvae by the capsules indicates that this method of treatment is likely to prove extremely effective against type 2 Ostertagiasis, particularly when the timing of the dosing related to the expected time of outbreak of the larvae is most probably less crucial in the case of capsules.

EXAMPLE 5

The capsules of Example 4 were filled with a matrix consisting of stearic acid (50%) polyethyleneglycol M.W.=6000 (15%) and Teric 16A29 (35%) containing suspended Oxfendazole (1.25%). Capsules released Oxfendazole at the rate shown in Table 3.

TABLE 3

| Time, day | Release of Oxfendazole mg/kg/day |
| --- | --- |
| 5 | 0.23 |
| 10 | 0.16 |
| 15 | 0.13 |
| 10 | 0.12 |
| 25 | 0.10 |

5 naturally infested steers were treated with capsules, and fecal egg counts were taken weekly for 70 days. The animals were then removed and worm-free stock run on the same pasture to determine the extent of re-infestation from the pasture. The performance of the capsules was compared with a single dose of 2.5 mg/kg of bodyweight of Oxfendazole on the same day of treatment.

Fecal egg counts are given in Table 4.

TABLE 4

| Treatment | Days after Treatment | | | |
| --- | --- | --- | --- | --- |
| | up to 30 Fecal egg counts | 37 (Ostertagia) | 48 No/g | 54 wet weight |
| Capsule | ≃0 | <6 | <6 | <6 |
| 2.5 mg/kg | ≃0 | 10 | 27 | 10 |

EXAMPLE 6

Figure 4:
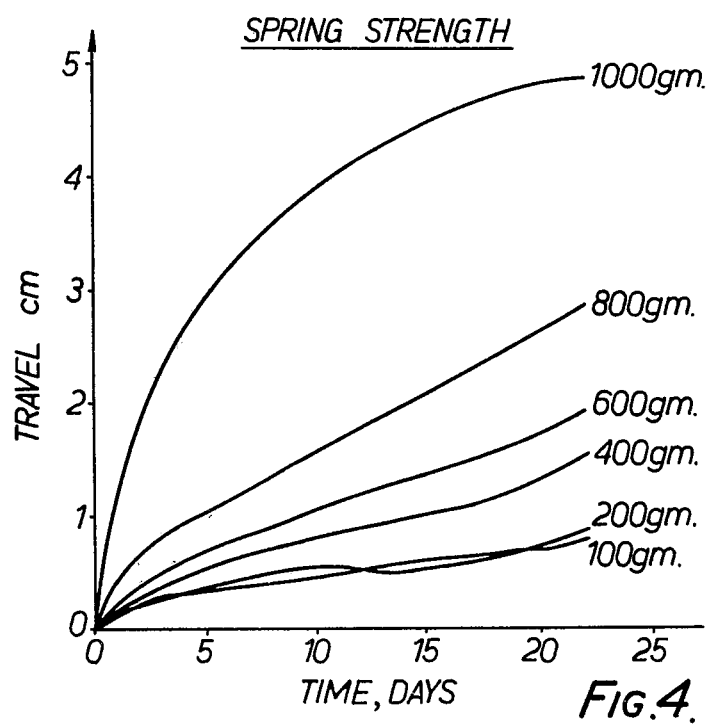

The influence of spring strength on extrusion rate for Teric 18M2:

Capsules as shown in FIG. 1 were prepared from Terumo (Trade Mark of Terumo Australia Pty. Ltd.) 10 ml polypropylene syringes of 1.5 cm I.D. and 10 cm length with a cylindrical core of Teric 18M2 1.48 cm diameter and 7 cm long. Springs 24 cm long were used to hold the cores against a 0.7×0.7 cm cylindrical orifice. The springs had a force of 100, 200, 400, 600, 800, 1000 g at a compressed length of 6 cm. The spring chamber of the capsules were open to the outside. In vivo release is illustrated in FIG. 4.

EXAMPLE 7

Figure 5:
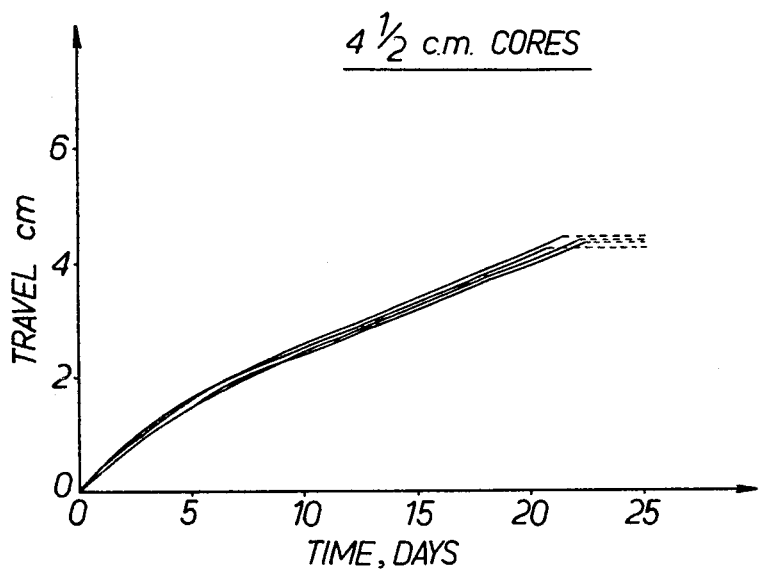

Release by extrusion of water-swollen matrix:

Capsules were made of 10 ml Terumo-syringes and contained cylindrical cores of Teric 18M2 plus 8% Mebendazole (Trade Mark of Johnson & Johnson). 24 cm springs with a force of 160 g at a compressed length of 6 cm held the cores against a restraining bar 1.2 mm wide across the diameter of the open end of the capsule. In vivo release from four capsules is shown in FIG. 5.

EXAMPLE 8

Differential dissolution of Teric 16A29 (Trade Mark of I.C.I. Australia Ltd.) from a matrix of stearic acid (56%) plus Teric 16A29 (44%):

A capsule was prepared as described in Example 7, except that the cylindrical core was made of Stearic acid (56%) and Teric 16A29 (44%). The capsule showed a constant rate of release in vivo for 26 days and then stopped. The core was initially 6.5 cm long, and this was reduced to 3.6 cm at the time of removal and disassembly. The core was divided into three equal cylinders, being the front, middle and rear portions of the core. These were analysed for stearic acid and calcium stearate. Results are given in Table 5.

TABLE 5

| | Free Stearic Acid | Acid as Ca Salt | Total Acid |
| --- | --- | --- | --- |
| Before use | 56% | 0 | 56% |
| Front | 86.1% | 10.6% | 96.7% |
| Middle | 86.5% | 5.1% | 91.6% |
| Rear | 82.1% | 3.8% | 85.9% |

EXAMPLE 9

Figure 6:
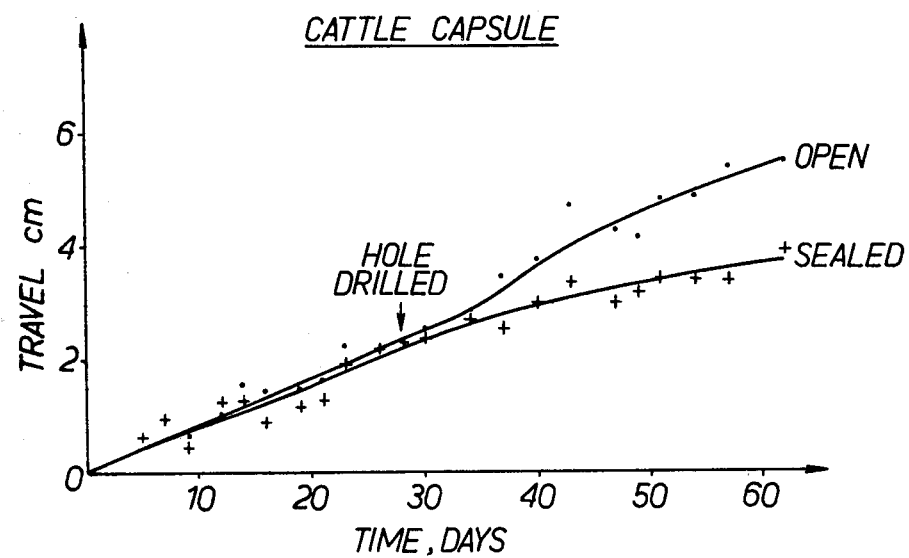

Evidence of the rate-limiting effect of gas diffusion on in vivo release:

Two capsules were prepared from 50 ml Terumo syringes, of 2.9 cm I.D. and 13 cm length. Cores of Teric 18M2 2.84 cm diameter and 11 cm long were inserted and held against shoulders at the open ends of the capsules by the action of 36 cm springs with a 160 g force at a compressed length of 9 cm. The spring chambers were sealed. In vivo release is shown in FIG. 6. At 28 days in the cow, one capsule was removed, a 6 mm diameter hole drilled into the spring chamber, and the capsule re-inserted. The increased rate of release following the opening of the spring chamber is evident in FIG. 6.

EXAMPLE 10

This example shows the use of the spring driven, controlled release capsule for the administration of Monensin sodium (Eli Lilly & Co.) a growth stimulant for cattle.

30 spayed Hereford heifers were treated with capsules in accordance with the invention containing Monensin (24% w/w) in a matrix of Teric 18M2. Trials, in July 1977, were run with 30 equivalent untreated cattle as controlled. The pasture was subterranean clover plus rye grass and other grasses and was high in soluble protein but low in available energy. The capsules released 200 mg/dose for 100 days and the trial duration os 63 days.

The capsules also contained chromium EDTA labelled with radio active $^{51}$Cr, a fecal dry matter marker to measure pasture consumption rates. 10 of the untreated controls also received a capsule containing the marker material only. Bodyweights were measured before and after the trial period and the results were as follows:

| Group | $^{51}$Cr-Chromium EDTA Bodyweight Gain ± S.E.M. | Fecal Dry Matter Output* |
| --- | --- | --- |
| Controls | 17.2 ± 3.2 kg (0.27 ± 0.02/day) | 12.31 ± 0.94 |
| Treated | 18.6 ± 4.0 kg (0.45 ± 0.03/day) | 8.05 ± 0.97 |

*Units g dry matter/kg live weight/day

Both the body weight gains and fecal dry matter outputs were significantly influenced by the treatment (p<0.01).

I claim:

1. In a controlled release composition for administering active agents to ruminants, comprising an effective amount of an active agent, up to about 50% by weight based on the total weight of the composition, in a matrix of a biologically acceptable water insoluble wax and a biologically acceptable surfactant; the improvement in said matrix comprising at least two surfactants having an HLB value of 8.5 or less, the HLB values of said surfactants differing by not more than 2 units thereby avoiding differential dissolution and non-uniform active agent release rate arising from the component with the higher HLB value diffusing faster than the component with the lower HLB value, said composition comprising the improved matrix having a melting point in excess of 39° C. and, when inserted as a solid into the rumen of a ruminant, having the property of controlled slow disintegration at the interface between said composition and ruminal fluid in the rumen of said ruminant.

2. A composition according to claim 1, wherein the composition is capable of disintegrating at a rate in the range from 0.01 cm/day to 0.3 cm/day.

3. A composition according to claim 1, wherein the composition is capable of imbibing moisture from said ruminal fluid to cause said composition to swell at the interface thereby rendering it susceptible to disintegration.

4. A composition according to claim 1, wherein said surfactants are selected from the group consisting of sorbitan monostearate, sorbitan mono-oleate and stearyl alcohol ethoxylated with 2 moles of ethylene oxide.

5. A composition according to claim 1 comprising about 80% by weight of sorbitan monostearate and about 20% by weight of stearyl alcohol ethoxylated with 2 moles of ethylene oxide.

6. A therapeutic composition according to claim 1 wherein the therapeutic composition contains no more than 12 to 15% by weight of the therapeutic agent.

7. A therapeutic composition according to claim 1, wherein said therapeutic composition comprises layers of the therapeutic composition interposed between layers of said controlled release composition containing little or no therapeutic agent.

8. A therapeutic composition according to claim 1, wherein the therapeutic agent is oxfendazole.

9. A method of treating ruminants with a therapeutic composition according to claim 1, which method comprises administering said therapeutic composition to ruminants in such a manner that the composition is not regurgitated until substantially all said therapeutic composition has disintegrated.

* * * * *